United States Patent
Bauer et al.

(10) Patent No.: US 6,487,922 B1
(45) Date of Patent: Dec. 3, 2002

(54) STEAM TURBINE INLET SLEEVE INSPECTION APPARATUS AND METHOD

(75) Inventors: James A. Bauer, Gibsonia, PA (US); Michael J. Metala, Murrysville, PA (US); Charles C. Moore, Hibbs, PA (US); George F. Dailey, Pittsburgh, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 148 days.

(21) Appl. No.: 09/669,783

(22) Filed: Sep. 25, 2000

(51) Int. Cl.7 .............................................. G01N 29/10
(52) U.S. Cl. .................... 73/865.8; 74/420; 74/457; 74/458; 74/459.5; 74/460; 356/3.03
(58) Field of Search ............................ 73/865.8, 866.1, 73/866.3, 866.5, 86, 618, 633, 151

(56) References Cited

U.S. PATENT DOCUMENTS

| | | | | |
|---|---|---|---|---|
| 2,453,656 A | * | 11/1948 | Bullard, II .................... 74/109 |
| 3,817,089 A | * | 6/1974 | Eggleton et al. ............. 335/206 |
| 3,907,308 A | | 9/1975 | Stock ........................... 277/503 |
| 3,922,907 A | | 12/1975 | Hurwitz et al. ................ 73/642 |
| 3,969,929 A | * | 7/1976 | Shaw et al. ............... 73/152.59 |
| 4,388,831 A | | 6/1983 | Sherman ....................... 73/623 |
| 4,597,294 A | * | 7/1986 | Brill et al. .................... 376/252 |
| 4,741,203 A | | 5/1988 | Willaman et al. .............. 73/116 |
| 4,802,679 A | | 2/1989 | Chen et al. ................... 277/637 |
| 4,806,863 A | | 2/1989 | White ........................... 324/238 |
| 4,808,924 A | | 2/1989 | Cecco et al. .................. 324/220 |
| 4,811,091 A | | 3/1989 | Morrison et al. ............... 348/83 |
| 4,812,105 A | | 3/1989 | Heymann ..................... 415/134 |
| 4,856,337 A | | 8/1989 | Metala et al. .................. 73/601 |
| 4,955,235 A | | 9/1990 | Metala et al. .................. 73/601 |
| 5,025,215 A | | 6/1991 | Pirl .............................. 324/220 |
| 5,105,876 A | | 4/1992 | Burack et al. ............... 165/11.2 |
| 5,140,264 A | | 8/1992 | Metala et al. ................ 324/219 |
| 5,142,230 A | | 8/1992 | Nottingham ................. 324/262 |
| 5,146,786 A | | 9/1992 | Nachbar ........................ 73/623 |
| 5,164,826 A | | 11/1992 | Dailey ........................... 348/83 |
| 5,333,502 A | | 8/1994 | Clark, Jr. et al. .............. 73/623 |
| 5,408,883 A | * | 4/1995 | Clark et al. .................. 29/33 T |
| 5,442,285 A | | 8/1995 | Zombo et al. ............... 324/227 |
| 5,484,260 A | | 1/1996 | Brandon ...................... 415/134 |
| 5,563,357 A | | 10/1996 | Longree .................... 73/866.5 |
| 5,635,780 A | | 6/1997 | Kohlert et al. ............ 310/68 R |
| 5,670,879 A | | 9/1997 | Zombo et al. ............... 342/227 |
| 5,686,674 A | * | 11/1997 | Lowry et al. ............... 73/865.8 |
| 5,997,249 A | | 12/1999 | Bell ........................ 415/173.5 |

* cited by examiner

*Primary Examiner*—Hezron Williams
*Assistant Examiner*—David Rogers

(57) ABSTRACT

An inspection apparatus (40) for remote inspection of the trepan radius area (34) of the inlet sleeve (24) of a steam turbine (10). The apparatus (40) provides a sealed volume (50) between a pair of inflatable bladders (46,48) for the introduction of a liquid couplant for the immersion of ultrasonic transducers (42,44). A laser line generator (62) generates a beam of light visible through camera (60) which impinges upon the inlet bell seal (30) when the apparatus (40) is in a proper inspection position within the inlet sleeve (24). Guide vanes (56) provide centering and generate an insertion force during air assisted insertion of apparatus (40). Transducers (42,44) are indexed axially and circumfretially by the independent rotation of axial drive gear (72) and longitudinal drive gear (70) engaged with a pattern of gear teeth (69) formed as a combination of circumferential spur gear teeth and axial rack gear teeth cut into a single surface of a spline shaft (68).

10 Claims, 5 Drawing Sheets

STEAM TURBINE INLET SLEEVE INSPECTION APPARATUS AND METHOD

BACKGROUND OF THE INVENTION

This invention relates generally to the field of non-destructive examination, and more specifically to the non-destructive examination of portions of a steam turbine apparatus, and particularly to an apparatus and method for the remote inspection of the inlet sleeve area of a high pressure steam turbine.

Steam turbines are well known in the power generation industry. A steam turbine is a device operable to extract heat energy from a flow of high pressure, high temperature steam and to convert that heat energy into mechanical energy in the form of the rotation of a shaft. The steam flow may be generated by any known type of steam generator, such as for example a fossil fueled boiler or a nuclear powered steam supply system. The rotating shaft of the turbine is commonly connected to a rotor shaft of an electrical generator to further convert the mechanical energy of the rotating shaft into electrical energy for distribution via the electrical power grid.

A typical steam turbine is illustrated in FIG. 1. The steam turbine 10 includes a rotor shaft 12 journaled for rotation within an inner cylinder 14 and an outer cylinder 16. The inner cylinder 14 includes, among other parts, a blade carrier ring 18 and several nozzle chamber units 20 each welded to the inner cylinder so as to become an integral part thereof. The outer cylinder 16 includes one or more high pressure steam inlets 22 and a number of inlet sleeve units 24, each of which extends inwardly in telescoping relation to its associated nozzle chamber 20 in the inner cylinder 14. Steam enters the turbine inlet 22 from a high pressure steam line (not shown) downstream from one or more control valves (not shown), into a nozzle chamber 20 integrally attached to the inner cylinder 14. The steam then passes through the nozzle and control stage rotating blades 26 that are attached to the rotor shaft 12. Steam from several parallel inlet paths flows into a control stage chamber 27 and around the various nozzle units 20 to merge together to flow through the remainder of the turbine array of stationary 28 and rotating 29 blade rows. The expanded steam exiting the last blade row enters a steam outlet annulus 36 formed between the inner and outer cylinders 14, 16 and is directed to an outlet 38.

The inlet steam flow must pass between the inner and outer cylinders 14, 16 without leakage between the cylinders. This requires a static seal that will withstand extremely high pressures, high temperatures, and differential thermal expansion. The seal must be substantially fluid tight and stable under conditions of extremely high velocity and sometimes pulsating steam flow. Dynamic instability, vibration and thermal shock are repeatedly encountered in use by the seal assembly. It is know to use a bell seal 30 for this application. Several known designs of such bell seals are described in U.S. Pat. No. 3,907,308 dated Sep. 23, 1975; U.S. Pat. No. 4,802,679 dated Feb. 7, 1989; and U.S. Pat. No. 4,812,105 dated Mar. 14, 1989.

Reliable operation of a steam turbine is desired in order to ensure the integrity of the electrical power supply and to avoid unplanned, and therefore more costly, repairs resulting from failures during the operation of the turbine. A variety of routine inspections are performed on a steam turbine to assess the condition of the machine during its useful operating life, and to detect degraded conditions before they mature into a part failure. The inlet sleeve area of a turbine is subject to extremes of temperature, thermal shock, vibration, and differential expansion, and as such, is an area vulnerable to mechanical wear and cracking. In particular, it is known that the surface 32 of the inner cylinder 14 in contact with the bell seal 30 is subject to wear. Such wear can result in a decrease in the effectiveness of the bell seal 30 and a greater leakage between the inner cylinder 14 and the outer cylinder 16 than desired. Furthermore, the trepan radius area 34 of the outer cylinder inlet sleeve 24 has been known to develop high cycle fatigue cracks in some turbines. It is known to inspect portions of a steam turbine by inserting a miniature camera into the turbine through the main steam inlet nozzle 22, such as is taught by U.S. Pat. No. 5,164,826 dated Nov. 17, 1992. However, inspections of the bell seal and trepan radius areas 30, 34 have previously been performed with the turbine out of service and with the turbine casing disassembled to provide access to these parts. Consequently, these inspections are time consuming and expensive.

Once the turbine is disassembled, the bell seal 30 may be visually inspected and measured for wear. The trepan radius area 34 is, however, too restricted to permit a reliable visual inspection. It is known to inspect this area with a special magnetic rubber material. The trepan radius area 34 must first be cleaned of accumulated scale and dirt such as by grit blasting. Special bladders are inserted into the trepan groove 35 to provide a sealed cavity therein. A multi-loop coil is wrapped around the outside of the inlet sleeve 24, and a liquid magnetic rubber material is then pumped into the sealed cavity. An electrical current is passed through the multi-loop coil to produce a magnetic field within the inlet sleeve 24. Cracks in the trepan area 34 will act as flux leakage sites and will draw small magnetic particles in the liquid magnetic rubber material toward the flux leakage sites. As the liquid rubber solidifies, this build up of magnetic particles is captured and can be interpreted as an indication of cracks in the trepan area 34 by a skilled non-destructive examination technician. This type of inspection is generally performed only during scheduled turbine maintenance outages when the turbine is being disassembled for other purposes, and the information provided about flaws in the trepan radius area is affected by the inherent limitations of electromagnetic testing techniques.

BRIEF SUMMARY OF THE INVENTION

Thus there is a particular need for an inspection technique that provides an improved non-destructive examination of the turbine inlet sleeve area without the need for the disassembly of the turbine.

Accordingly, a method of inspecting the inlet sleeve area of a steam turbine is described herein, the method comprising the steps of: providing an inspection tool adapted for insertion into a steam inlet of the steam turbine, the inspection tool including a spaced pair of inflatable bladders and an ultrasonic transducer disposed there between; inserting the inspection tool into the steam inlet and moving it into an inspection position proximate the inlet sleeve; pressurizing the pair of inflatable bladders to form a sealed area surrounding the ultrasonic transducer; introducing liquid couplant into the sealed area; operating the ultrasonic transducer to perform a non-destructive examination of the inlet sleeve area; depressurizing the pair of inflatable bladders; and withdrawing the inspection tool from the steam inlet. The method may further include the steps of: providing a source of light and a camera on the inspection tool; and monitoring the output of the camera during the step of inserting the inspection tool to identify the inspection position when light produced by the source of light impinges upon a predetermined structure proximate the inspection tool.

An apparatus for implementing the disclosed method of inspecting the inlet sleeve of a turbine is also described. The apparatus includes a guide tube adapted for insertion into a steam line connected to a turbine; an ultrasonic transducer movably connected about an inspection section of the guide tube for remote operation of the transducer; an actuator connected between the guide tube and the ultrasonic transducer for selectively and remotely moving the transducer relative to the inspection section for inspecting a surrounding structure; a leading inflatable bladder and a trailing inflatable bladder each attached about the guide tube on opposed sides of the inspection section; and a couplant supply line having an opening between the leading and trailing inflatable bladders for selectively and remotely providing couplant to a volume between the leading and trailing bladders including the ultrasonic transducer. The apparatus may also include an optical positioning device attached to the guide tube for providing a remote indication of the position of the inspection section. The optical positioning device may be a laser for projecting a beam of light; and a camera for remotely monitoring the location of impingement of the beam of light.

A tool for providing both axial and rotational movement of the ultrasonic transducer in the inspection apparatus may include a shaft having an axis; a pattern of spur gear teeth formed on a first portion of the surface of the shaft, the pattern of spur gear teeth formed in a circumferential direction about the surface of the shaft; a pattern of rack gear teeth formed on the first portion of the surface of the shaft, the pattern of rack gear teeth formed in a longitudinal direction about the surface of the shaft; a driven oscillator gear engaged with the pattern of spur gear teeth for imparting rotation of the shaft about the axis; and a driven axial spur gear engaged with the pattern of rack gear teeth for imparting axial movement of the shaft along the axis.

BRIEF DESCRIPTION OF THE DRAWINGS

The features and advantages of the present invention will become apparent from the following detailed description of the invention when read with the accompanying drawings. Like structures illustrated in more than one figure are numbered consistently among the figures.

DETAILED DESCRIPTION OF THE INVENTION

Figure 1:
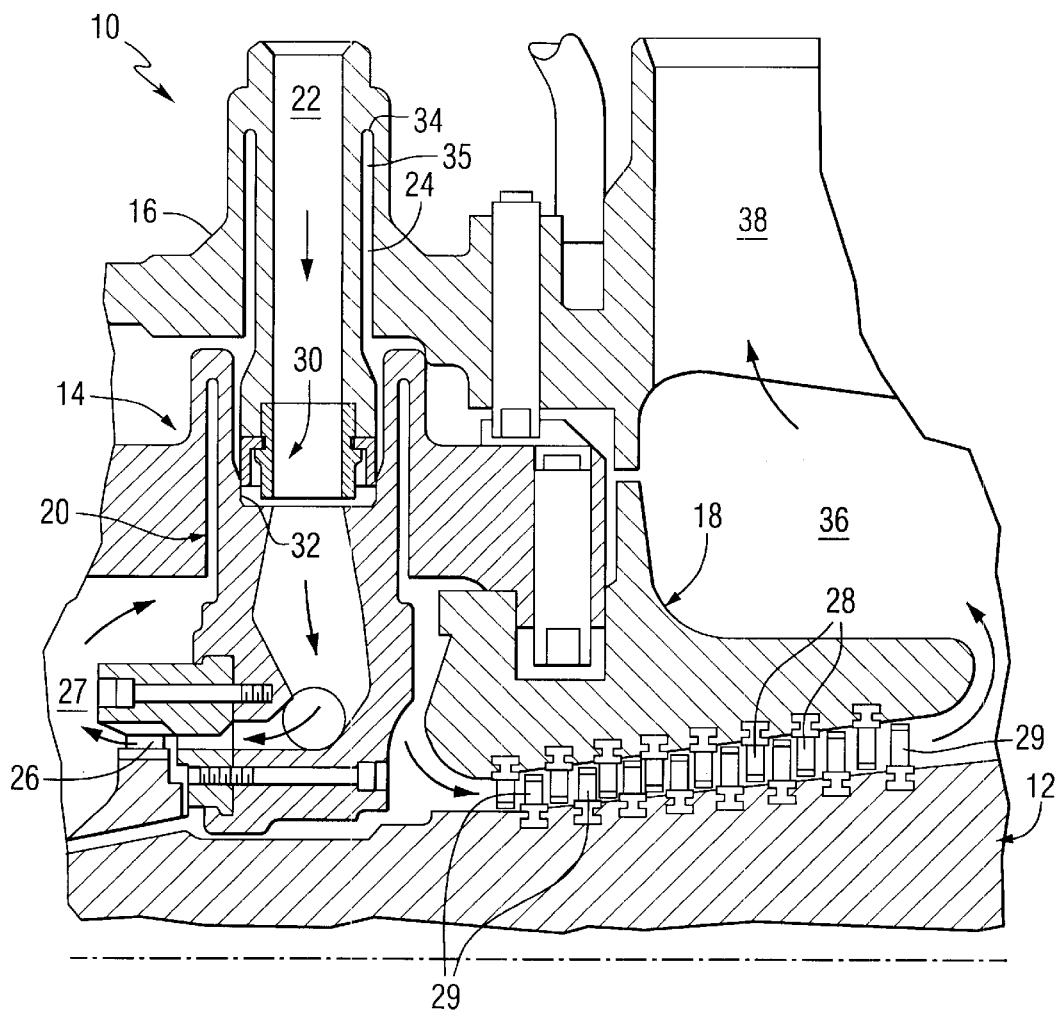
FIG. 1 is a partial cross-sectional view of a prior art steam turbine showing the major elements of the turbine including the inlet sleeve trepan area and the bell seal.
Figure 2:
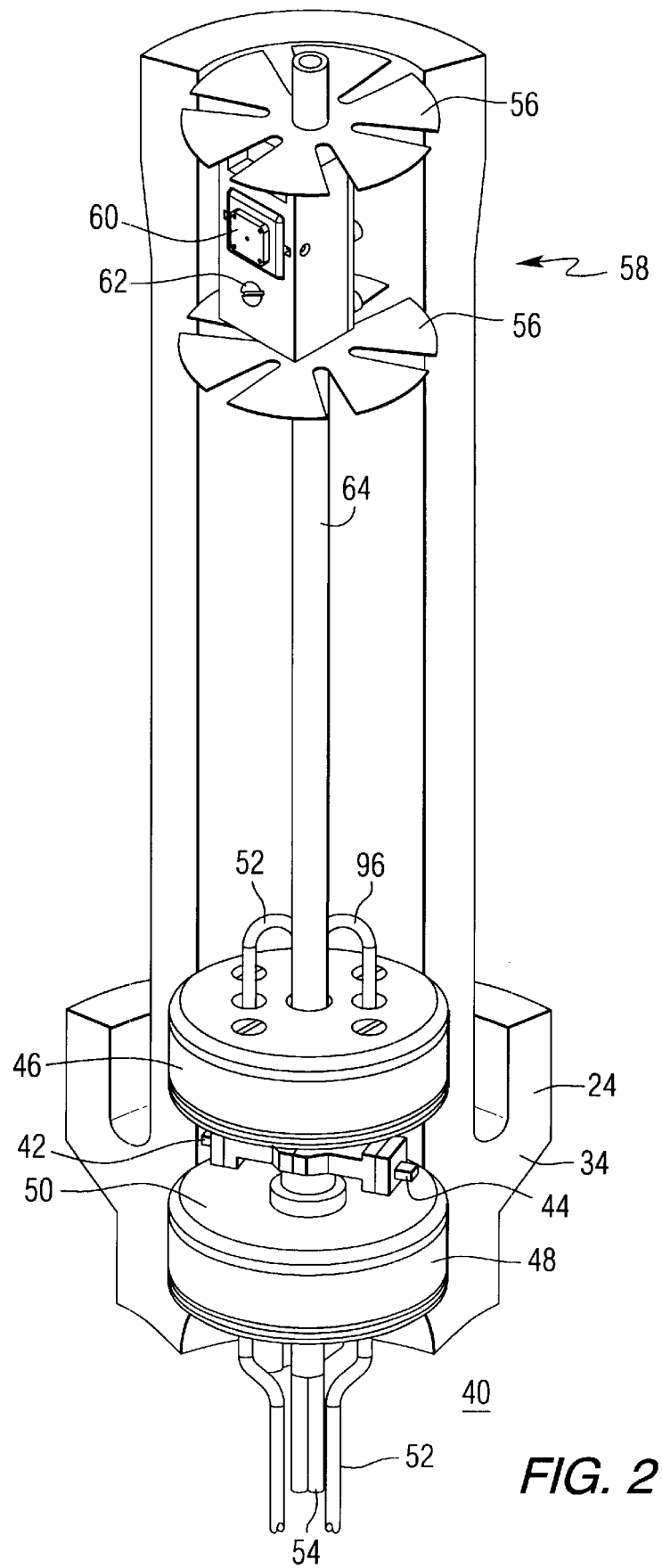
FIG. 2 is a perspective view of an inspection tool positioned in the inlet sleeve area of a steam turbine.

FIG. 2 is a perspective view of an inspection tool apparatus 40 used for inspecting the inlet sleeve 24 of a steam turbine 10. Apparatus 40 is adapted for insertion into the steam inlet 22 of steam turbine 10 as illustrated in FIG. 1.

Figure 3:
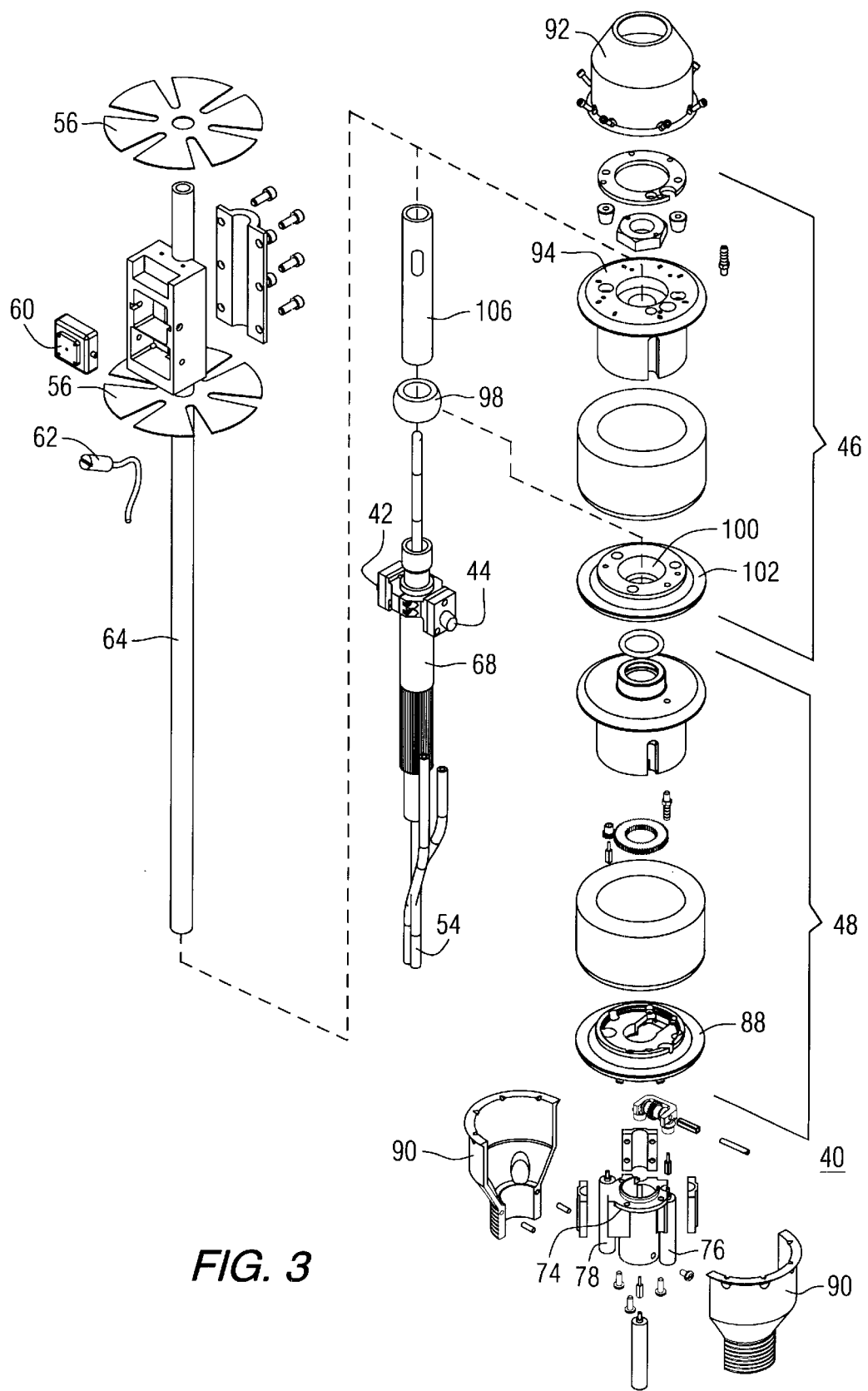
FIG. 3 is an exploded view of the inspection tool of FIG. 2.
Figure 4:
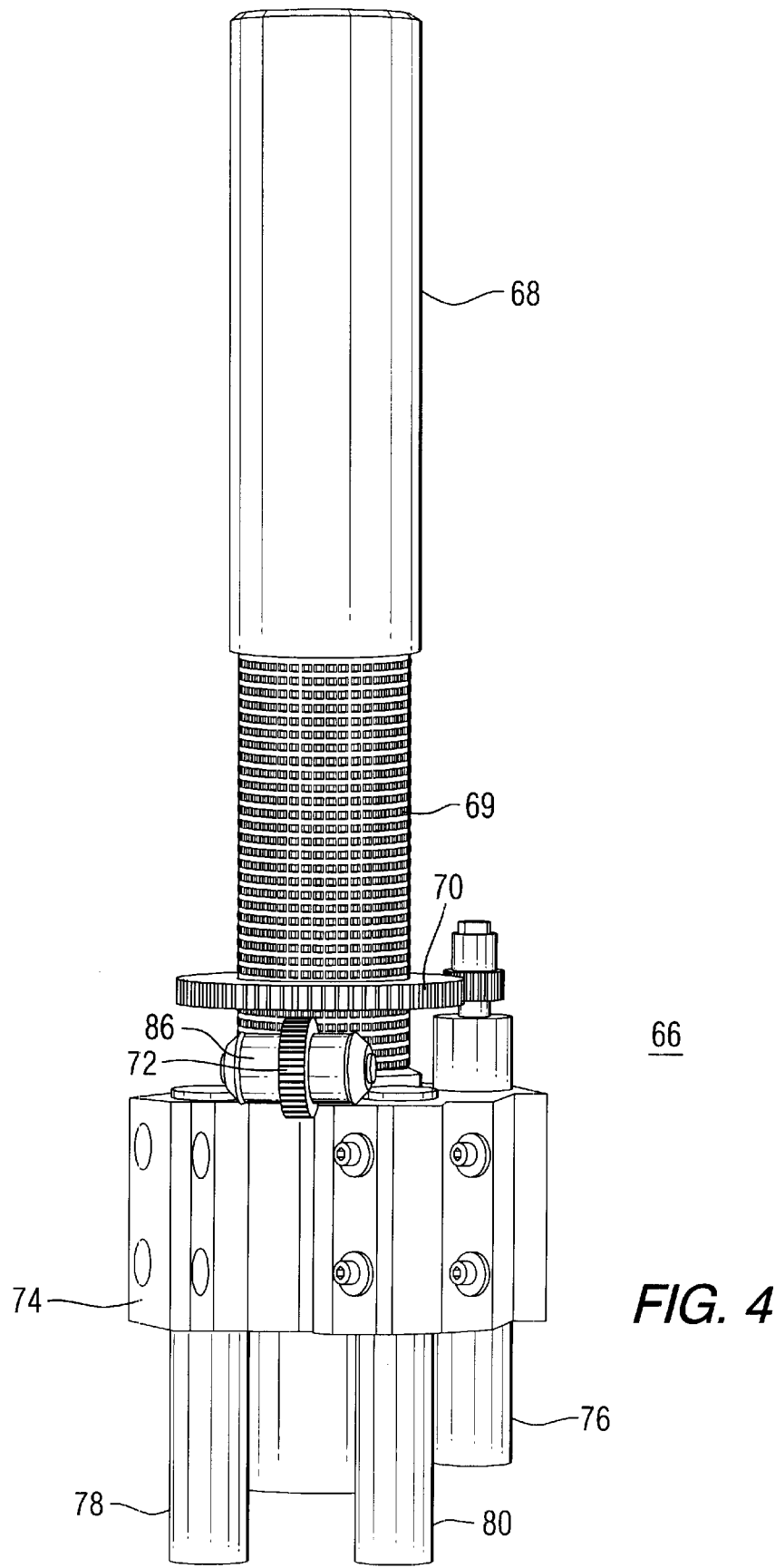
FIG. 4 is a more detailed view of a portion of the inspection tool of FIGS. 2 and 3 showing the mechanism used to provide axial and circumferential movement of the ultrasonic transducers.

FIG. 3 illustrates an exploded view of the various parts of the inspection apparatus 40, and FIG. 4 illustrates a more detailed view of a drive mechanism portion of the apparatus 40. The following description may be best understood when viewing FIGS. 2–4 together.

Apparatus 40 includes a non-destructive testing apparatus capable of facilitating the remote inspection of the trepan radius area 34 of inlet sleeve 24. In the embodiment illustrated, the non-destructive examination apparatus consists of two ultrasonic transducers 42, 44 adapted to perform an inspection of the inlet sleeve 24. One or more ultrasonic transducers 42, 44 may be provided to perform any variety of known ultrasonic examinations, such as longitudinal and shear wave examinations. An appropriate examination procedure in accordance with known ultrasonic testing techniques may be developed to measure the wall thickness, to confirm the correct location of the inspection tool 40, to detect cracks, and/or to provide information regarding crack size. Ultrasonic transducers 42, 44 are illustrated as immersion style devices, as will be described more fully below. Alternatively, contact transducers may be used for performing an ultrasonic inspection. Additionally, other types of non-destructive examination devices may be employed, such as an electromagnetic acoustic transducer (EMAT), eddy current transducer, remote field eddy current sensors, infrared sensors, etc. The non-destructive examination device mechanically attached to tool 40 is electrically or optically attached to an appropriate electronics system (not shown) located outside of the turbine. A qualified technician may thereby remotely operate the in-situ transducer to perform an inspection of the inlet sleeve 24 without the need for the disassembly of the turbine 10. The applicant has found that immersion ultrasonic transducers illustrated provide a preferred method of examination for the illustrated application.

A leading air bladder 46 and a trailing air bladder 48 are disposed on opposed sides of the ultrasonic transducers 42, 44. When inflated, bladders 46, 48 define a sealed volume 50 surrounding the ultrasonic transducers 42, 44 within the bore of the inlet sleeve 24. Liquid couplant (not shown) may be introduced into and drained from this sealed volume 50 by one or more couplant supply lines 52 having an opening into sealed volume 50. The leading and trailing bladders 46, 48 are attached directly or indirectly to a guide tube 54 that is adapted for insertion into a steam line connected to the turbine 10. The guide tube 54 may be extended to a length sufficient to move the apparatus 40 from an access port in the steam line, such as a disassembled main steam valve, to the area of the inlet sleeve 24 to be inspected. Alternatively, guide tube 54 may be connected directly or indirectly to a flexible conduit or other means for inserting the apparatus into the turbine. In one embodiment a hollow flexible conduit is used with a thin, flexible fiberglass rod for providing sufficient pushing force to insert the apparatus 40. One or more guide vanes 56 may be attached directly or indirectly to the guide tube 54 in order to center the inspection tool 40 within the bore of the inlet sleeve 24, and also to serve as a sail during air-assisted installation of the tool 40 into the turbine 10. By blowing air over the guide vanes during the insertion of the inspection tool into the turbine 10, a force is created against the guide vanes 56 in the direction of movement of the inspection tool 40. This force may be sufficient alone or may be used in conjunction with a pushing force applied directly to the guide tube 54 or attached flexible conduit. The tool 40 may be withdrawn from the turbine 10 by pulling on the guide tube 54 or attached flexible conduit. Although not shown, a strong flexible cable, such as a stranded metal aircraft cable, may be attached to the leading guide vane 56 in order to provide a fail safe mechanism for the retrieval of all parts of apparatus 40 from the turbine 10.

Inspection apparatus 40 may be positioned at a desired inspection position by the operation of an optical positioning device 58 attached directly or indirectly to the guide tube 54. The optical positioning device is illustrated as including a miniature CCTV camera 60 positioned proximate to a laser line generator 62. The laser 62 projects a beam of light onto the structure adjacent the inspection apparatus 40. The miniature camera 60 is operable to provide a remote image on a monitor located outside the turbine showing the point of impingement of the laser light beam onto the surrounding structure. The laser 62 is positioned to be a predetermined distance from the ultrasonic transducers 42, 44 by a hollow flex tube 64 having a predetermined length. The distance between the laser 62 and the non-destructive examination apparatus is selected as a function of the distance between a known structure visible from within the bore of the inlet of the steam turbine 10 to an area of the inlet sleeve 24 to be inspected. For example, the distance between the bell seal 30 and the trepan area 34 of the inlet sleeve 24 is a known dimension. The distance between the laser line generator 62 and the ultrasonic transducers 42, 44 may be selected so that the ultrasonic transducers 42, 44 are positioned proximate the area to be inspected when light produced by the laser 62 impinges upon the retaining nut holding the bell seal in the steam turbine 10.

The application of most types of non-destructive examination devices to a tubular shaped product requires the movement of the transducer relative to the area to be inspected. Inspection apparatus 40 includes a mechanism 66 illustrated in FIG. 4 for providing both axial and rotational movement. A spline shaft 68 has a top generally smooth portion to which are attached the ultrasonic transducers 42, 44. Shaft 68 is generally hollow and fits over an inspection section of the guide tube 54. A bottom portion of the surface of the shaft 68 is provided with a pattern of gear teeth 69. The gear teeth are formed by combining a pattern of spur gear teeth formed in a circumfractial direction about the surface of the shaft 68, and a pattern of rack gear teeth formed in a longitudinal direction above the surface of the shaft 68. Such a double pattern of gear teeth may be manufactured using standard cutters for both the spur gear teeth and the rack gear teeth. For example, a pattern of spur gear teeth may first be formed around the full circumference of shaft 68 using standard cutters. A CNC machining center may then be fitted with a standard rack gear cutter for the machining of the pattern of rack gear teeth. In lieu of the standard operation of holding a shaft motionless while a rack gear tooth cutter is past tensionally across the surface of the shaft, the shaft 68 is rotated about its longitudinal axis as the rack gear cutter is held against the surface of the shaft 68. After one complete rotation of the shaft about its axis, the cutter is indexed axially to a second tooth position and the process is repeated. In this manner, a pattern of gear teeth is formed on the spline shaft 68 that will provide a reaction surface for both an oscillator gear 70 and an axial drive gear 72. Oscillator gear 70 has an inside diameter gear tooth pattern engaged with the spline shaft gear tooth pattern so as to prevent the relative circumferential rotation there between. However, oscillator gear 70 is free to move in an axial direction with respect to spline shaft 68. Similarly, axial drive gear 72 is formed with a gear tooth pattern on its outside diameter for engagement with the combination gear tooth pattern 69 on the spline shaft 68 to provide engagement in the axial direction while allowing axial drive gear 72 to be rotated around the circumference of spline shaft 68. A motor mounting bracket 74 is attached directly or indirectly to the guide tube 54, and serves as a base for the mounting of oscillator motor 76 and axial drive motors 78, 80. The output of oscillator motor 76 is engaged with the oscillator gear 70 for causing the relative rotational movement of the spline shaft 68 and its attached ultrasonic transducers 42, 44 relative to the motor mounting brackets 74 and guide tube 54. Similarly, the output of axial drive motors 78, 80 are each engaged with the axial drive gear 72 through a respective pair of bevel gears connected to a shaft 86 which is in turn connected to the axial drive gear 72. Dual axial drive motors 78, 80 are utilized to increase the amount of available torque for driving the axial drive gear 72. Because of the mechanical advantage provided by oscillator gear 70, only a single oscillator motor 76 is utilized in this embodiment, however one may envision other applications where a polarity of oscillator motors may be used.

FIG. 3 illustrates an exploded view of the various components of inspection tool 40. Motor mounting plate 74 is attached to the bottom spindle plate 88 of trailing bladder assembly 48. A bottom cone 90 also is attached to the bottom spindle 88 and thereby indirectly to guide tube 54 and serves to provide an enclosure for motors 76, 78, 80. A top cone 92 attaches to a top spindle 94 of leading bladder assembly 46 in order to provide protection for liquid couplet hose 52, and leading bladder inflation hose 96 as may be seen in FIG. 2. A top portion of guide tube 54 is threaded into a ball 98 which is disposed in a socket recession 100 formed in a lower spindle plate 102 of leading bladder assembly 46. Ball 98 and socket 100 provide a flex joint in the guide tube 54 so that the hollow flexible tube 64 and optical positioning device 58 may pass through bends in the steam line. The top of a tube section 106 is threaded into the bottom of flex tube 64 and into the top spindle 94 of leading bladder 46. Various O-ring seals are provided to ensure that the liquid couplant is contained between bladders 42, 44 and does not leak around spline shaft 68 or guide tube 54.

The inlet sleeve area of a steam turbine may be inspected by providing an inspection tool 40 adapted for insertion into a steam inlet 22 of a steam turbine 10. The inspection tool 40 may be inserted into through an opened steam line valve through steam inlet 22 and moved into an inspection position proximate the inlet sleeve 24. The pair of bladders 46, 48 may then be inflated to form a sealed area 50 surrounding ultrasonic transducers 42, 44. A liquid couplet is introduced into the sealed area 50 through lines 52 and the ultrasonic transducers 42, 44 are operated to perform a non-destructive examination of the inlet sleeve area. Upon completion of the inspection, the couplet may be drained from the sealed area 50, and the bladders 46, 48 deflated to permit the withdrawal of the inspection tool 40 from the steam inlet 22. Correct positioning of the inspection tool 40 may be achieved by providing a source of light such as laser 62 and a remote viewing apparatus such as miniature camera 60 on the inspection tool 40, and monitoring the output of the camera during the step of inserting the inspection tool. The inspection tool 40 will be known to be in a desired inspection position when light produced by the laser 62 impinges upon a predetermined structure of the steam turbine 10 proximate the inspection tool 40. Insertion of the inspection tool 40 may be assisted by blowing compressed air against vanes 56 to create a force against the vanes in the direction of movement of the inspection tool 40.

Figure 5:
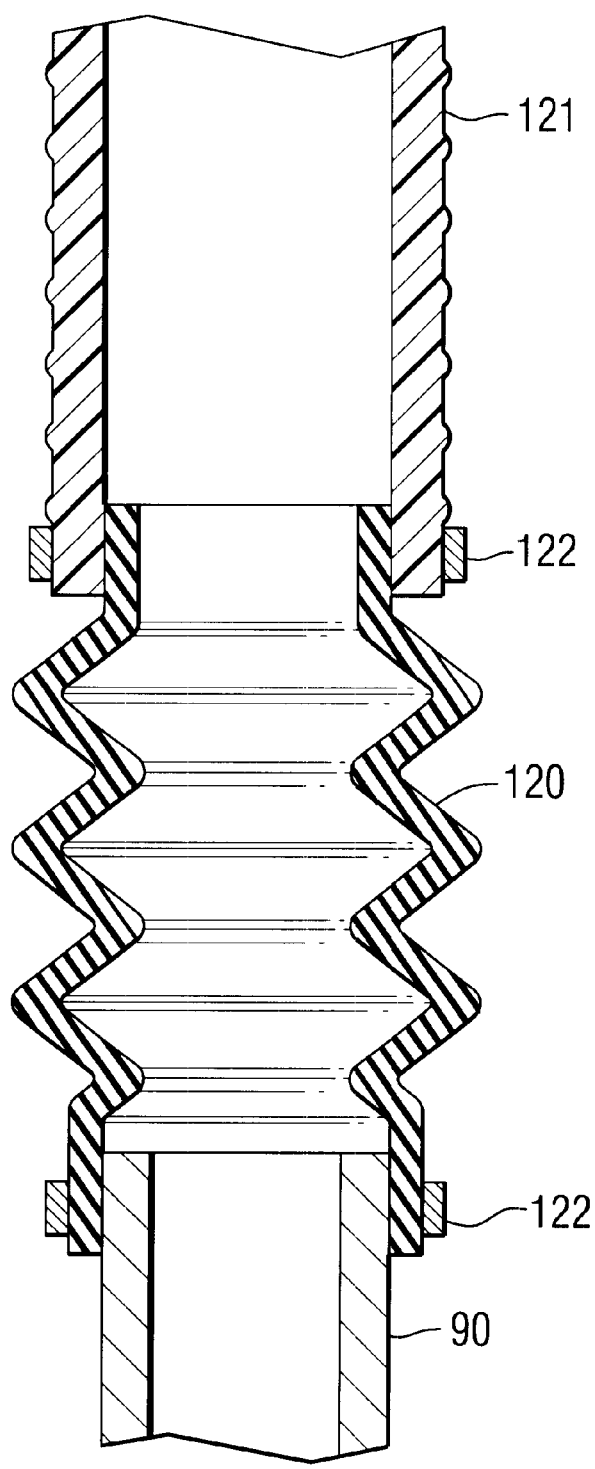
FIG. 5 is a sectional view of a flexible bellows member attached to the inspection tool of FIG. 2.

FIG. 5 is a device that facilitates the insertion of the inspection tool 40 into a turbine. A flexible, air tight bellows member 120 may be inserted between the bottom cone 90 attached to the guide tube 54 and a flexible conduit 121 used to push the tool 40 into a steam line. The flexible bellows member may be held in place by band clamps 122. The flexible bellows member 120 provides a means for flexing between the relatively rigid tool 40 and the guide tube 54, thereby allowing the tool 40 to more easily be inserted through bends in the steam line leading to the inlet 22 of the steam turbine 10. Bellows member may be formed of a rubber material having sufficient rigidity for positioning the bottom cone 90 relative to the flexible conduit 121, but with adequate flexibility provided by the bellows to allow bending as the tool 40 passes through a bend in the steam line.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

We claim as our invention:

1. An apparatus for inspecting the inlet sleeve of a turbine, the apparatus comprising:

a guide tube adapted for insertion into a steam line connected to a turbine;

an ultrasonic transducer movably connected about an inspection section of the guide tube;

an actuator connected between the guide tube and the ultrasonic transducer for selectively and remotely moving the transducer relative to the inspection section for inspecting a surrounding structure;

a leading inflatable bladder and a trailing inflatable bladder each attached about the guide tube on opposed sides of the inspection section;

a couplant supply line having an opening between the leading and trailing inflatable bladders for selectively providing couplant to a volume between the leading and trailing bladders including the ultrasonic transducer.

2. The apparatus of claim 1, further comprising an optical positioning device attached to the guide tube for providing a remote indication of the position of the inspection section.

3. The apparatus of claim 2, wherein the optical positioning device further comprises:

a laser for projecting a beam of light;

a camera for remotely monitoring the location of impingement of the beam of light.

4. The apparatus of claim 2, wherein the optical positioning device is attached to the guide tube at a predetermined distance from the inspection section, and further comprising a flex joint formed in the guide tube between the optical positioning device and the inspection section.

5. The apparatus of claim 4, wherein the flex joint is disposed proximate the leading inflatable bladder.

6. The apparatus of claim 1, further comprising:

a spline shaft disposed around a portion of the guide tube including the inspection section, the spline shaft being moveable in an axial direction and a rotation direction around the guide tube, the ultrasonic transducer being attached to the spline shaft;

a pattern of gear teeth formed on the outside surface of the spline shaft having both a rotationally oriented spur gear pattern and an axial rack gear pattern formed therein;

an oscillator gear engaged with the pattern of gear teeth for movement in a rotational direction;

an oscillator motor attached to the guide tube and having an output engaged with the oscillator gear for rotating the oscillator gear to cause rotational movement of the ultrasonic transducer relative to the guide tube;

an axial drive gear engaged with the pattern of gear teeth for movement in the axial direction;

an axial drive motor attached to the guide tube and having an output engaged with the axial drive gear for rotating the axial drive gear to cause axial movement of the ultrasonic transducer relative to the spline shaft.

7. The apparatus of claim 6, further comprising:

the axial drive gear comprising a spur gear having an attached shaft extending from opposed sides of the spur gear about an axis of rotation of the spur gear;

a bevel gear formed on each of opposed ends of the attached shaft;

a pair of axial drive motors attached to the guide tube and each having an output bevel gear engaged with a respective one of the bevel gears formed on the ends of the attached shaft.

8. The apparatus of claim 1, further comprising a straight beam ultrasonic transducer and a longitudinal beam ultrasonic transducer movably connected about an inspection section of the guide tube.

9. The apparatus of claim 1, further comprising a guide vane attached to the guide tube.

10. The apparatus of claim 1, further comprising:

a flexible member connected to the guide tube; and a flexible conduit attached to the flexible member for inserting the apparatus into the steam line.

* * * * *